(12) United States Patent
Ullah

(10) Patent No.: US 9,205,087 B1
(45) Date of Patent: Dec. 8, 2015

(54) 6-PIPERAZINYL-3,4-DIHYDROQUINAZOLIN-2(1H)-ONES

(71) Applicants: KING FAHD UNIVERSITY OF PETROLEUM AND MINERALS, Dhahran (SA); King Abdulaziz City for Science and Technology, Riyadh (SA)

(72) Inventor: Nisar Ullah, Dhahran (SA)

(73) Assignees: KING FAHD UNIVERSITY OF PETROLEUM AND MINERALS, Dhahran (SA); KING ABDULAZIZ CITY FOR SCIENCE AND TECHNOLOGY, Riyadh (SA)

( * ) Notice: Subject to any disclaimer, the term of this patent is extended or adjusted under 35 U.S.C. 154(b) by 0 days.

(21) Appl. No.: 14/848,058

(22) Filed: Sep. 8, 2015

Related U.S. Application Data

(63) Continuation of application No. 14/184,339, filed on Feb. 19, 2014, now Pat. No. 9,145,388.

(51) Int. Cl.
| | |
|---|---|
| C07D 239/80 | (2006.01) |
| C07D 401/12 | (2006.01) |
| A61K 31/517 | (2006.01) |
| A01N 43/54 | (2006.01) |

(52) U.S. Cl.
CPC ............... *A61K 31/517* (2013.01); *A01N 43/54* (2013.01)

(58) Field of Classification Search
CPC .. C07D 401/12; C07D 239/80; A61K 31/517; A01N 43/54
USPC ........................................ 514/266.2; 544/284
See application file for complete search history.

(56) References Cited

U.S. PATENT DOCUMENTS

| | | |
|---|---|---|
| 7,652,006 B2 | 1/2010 | Upasani et al. |
| 7,745,452 B2 | 6/2010 | Barrow et al. |
| 2010/0261741 A1 | 10/2010 | Barrow et al. |

FOREIGN PATENT DOCUMENTS

| | | |
|---|---|---|
| WO | 2010/090347 | 8/2010 |

*Primary Examiner* — Paul V Ward
(74) *Attorney, Agent, or Firm* — Oblon, McClelland, Maier & Neustadt, L.L.P.

(57) ABSTRACT

A series of new 6-piperazinyl-3,4-dihydroquinazolin-2(1H)-ones have been synthesized. The compounds are structurally related to adoprazine, a potential atypical antipsychotics bearing potent $D_2$ receptor antagonist and $5\text{-HT}_{1A}$ receptor agonist properties. Buchwald-Hartwig coupling of suitably modified aryl bromides with tert-butyl piperazine-1-carboxylate afforded the advanced intermediate piperazinyl-3,4-dihydroquinazolin-2(1H)-one. The reductive amination of the latter with appropriately designed biarylaldehydes accomplished the synthesis of these compounds.

6 Claims, 1 Drawing Sheet

6-PIPERAZINYL-3,4-DIHYDROQUINAZOLIN-2(1H)-ONES

CROSS REFERENCE TO RELATED APPLICATIONS

This application is a continuation application of U.S. application Ser. No. 14/184,339.

BACKGROUND OF THE INVENTION

1. Technical Field

The present invention relates to compounds having a basic bicyclic structure of a dihydroquinazolin compound and bearing $D_2$ receptor antagonist and 5-$HT_{1A}$ receptor agonist properties, a method of making the compounds, and a method for treating schizophrenia by administering an effective dose of one or more of the compounds.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Schizophrenia is a severe psychiatric illness afflicting 1% of the population worldwide. The diagnosis of the disease is based on diverse and variably expressed symptoms which can be grouped as positive and negative. The positive symptoms include disorganized thought, delusions and auditory hallucinations whereas the most characteristic negative symptoms are emotional flattening, poverty of speech and motivational deficits (Diagnostic and Statistical Manual of Mental Disorders. 4th ed., text revision, American Psychiatric Association, Washington, D.C., p. 297-343 (2000)—incorporated herein by reference in its entirety). FIG. 1 depicts the first-generation antipsychotics or typical antipsychotics such as chlorpromazine 1 and haloperidol 2. Both chlorpromazine 1 and haloperidol 2 are dopamine antagonists which alleviate positive symptoms including hallucinations, agitation and delusions but fail to control the negative symptoms such as blunted affect, emotional withdrawal and cognitive deficits. In addition these therapeutics develop extrapyramidal symptoms (EPS) and hyperprolactinemia, respectively (D. C. Goff, R. I. Shader. Non-neurological side-effects of antipsychotic drugs. In S. R. Hirsch, D. Weinberger, editors. Schizophrenia. 2nd ed., Blackwell Publishing, Oxford, p. 573-88 (2002)—incorporated herein by reference in its entirety) The 'second-generation' or atypical antipsychotics, such as clozapine 3, depicted in FIG. 1, combine $D_2$ receptor antagonism with activity at other receptors, on the premise that a suitable balance of pharmacological activity should broaden the spectrum of therapeutic efficacy and reduce EPS. With respect to classical neuroleptics, clozapine shows significantly greater efficacy, including an improved effect on negative symptoms, and causes a marked increase in dopamine output in the prefrontal cortex (H. Y. Meltzer, *Psychopharmacology*, 99, S18 (1989)—incorporated herein by reference in its entirety) Clozapine, however, is associated with its own set of serious side effects including weight gain, diabetes and an increased risk of seizures and agranulocytosis (L. H. Lindstrom, *Acta. Psychiatr. Scand.*, 77, 524 (1988)—incorporated herein by reference in its entirety)

Several preclinical observations suggest that combining 5-$HT_{1A}$ and $D_2$ receptor properties may provide a mutually complementary balance of pharmacological activity with reduced undesirable responses (E. P. Prinssen, F. C. Colpaert, W. Koek, *Eur. J. Pharmacol.*, 453, 217 (2002)—incorporated herein by reference in its entirety) Indeed, numerous mechanistic considerations (A. Newman-Tancredi, M. B. Assie, N. Leduc, A. M. Ormiere, N. Danty, C. Cosi, *Int. J. Neuropsychopharmacol.*, 8, 341 (2005); M. B. Assie, V. Ravailhe, V. Faucillon, A. Newman-Tancredi, *J. Pharmacol. Exp. Ther.*, 315, 265 (2005); L. A. B. Slot, L. D. Vries, A. Newman-Tancredi, D. Cussac, *Eur. J. Pharmacol.*, 534, 63 (2006)—each incorporated herein by reference in its entirety) and preclinical evidence (L. A. B. Slot, M. S. Kleven, *Neuropharmacology*, 49, 996 (2005); M. S. Kleven, C. Barret-Grevoz, L. A. B. Slot, A. Newman-Tancredi, *Neuropharmacology*, 49, 135 (2005); R. A. Bantick, J. F. W. Deakin, P. M. Grasby, *J. Psychopharmacol.*, 15, 37 (2001)—each incorporated herein by reference in its entirety) support the potential of such a combination. As a result, adoprazine 4 (SLV-313) and bifeprunox 5, bearing potent $D_2$ receptor antagonist and 5-$HT_{1A}$ receptor agonist properties, were developed as depicted in FIG. 1 (A. C. McCreary, J. C. Glennon, C. R. Ashby Jr, H. Y. Meltzer, Z. Li, J-H. Reinders, M. B. Hesselink, S. K. Long, A. H. Herremans, H. van Stuivenberg, R. W. Feenstra, C. G. Kruse, *Neuropsychopharmacology*, 32, 78 (2007)—incorporated herein by reference in its entirety)

The failure of 4 and 5 to oppose phencyclidine-induced social interaction deficits demonstrates the difficulty of balancing activity at these sites (A. Newman-Tancredi, *Curr. Opin. Invest. Drugs*, 11, 802 (2010)—incorporated herein by reference in its entirety) Compounds having effective ratios of $D_2$ and 5-$HT_{1A}$ activities are described herein (S. Cuisiat, N. Bourdiol, V. Lacharme, A. Newman-Tancredi, F. Colpaert, B. Vacher, *J. Med. Chem.*, 50, 865 (2007)—incorporated herein by reference in its entirety)

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the present invention includes a series of intermediate compounds having the basic bicyclic structure of a dihydroquinazolin compound.

In another embodiment, the series of intermediate compounds demonstrate $D_2$ receptor antagonist and 5-$HT_{1A}$ receptor agonist properties.

In another embodiment, the series of intermediate compounds have the piperazinyl moiety attached at the 6-position of the bicyclic dihydroquinazolin ring.

In another embodiment, 6-(4-(biphenyl-4-ylmethyl)piperazin-1-yl)-3,4-dihydroquinazolin-2(1H)-one is an intermediate compound.

In another embodiment, 6-(4-((4'-fluorobiphenyl-4-yl)methyl)piperazin-1-yl)-3,4-dihydroquinazolin-2(1H)-one is an intermediate compound.

In another embodiment, 6-(4-((5-phenylpyridin-3-yl)methyl)piperazin-1-yl)-3,4-dihydroquinazolin-2(1H)-one is an intermediate compound.

In another embodiment, 6-(4-((5-(4-fluorophenyl)pyridin-3-yl)methyl)piperazin-1-yl)-3,4-dihydroquinazolin-2(1H)-one is an intermediate compound.

In another embodiment, 6-(4-(3-cyclopentenylbenzyl)piperazin-1-yl)-3,4-dihydroquinazolin-2(1H)-one is an intermediate compound.

In another embodiment, 6-(4-((5-cyclopentenylpyridin-3-yl)methyl)piperazin-1-yl)-3,4-dihydroquinazolin-2(1H)-one is an intermediate compound.

In another embodiment, a method of making the series of intermediate compounds includes using Buchwald-Hartwig coupling a halogenized dihydroquinazolin-2(1H)-one with a tert-butyl piperazine-1-carboxylate.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
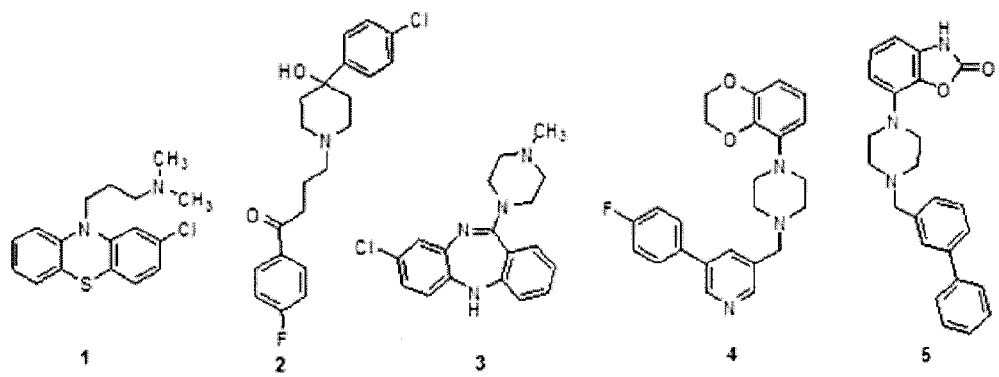
FIG. 1 displays compounds that bear 5-$HT_{1A}$ receptor agonist and $D_2$ receptor antagonist properties.

Referring now to the drawings, wherein like reference numerals designate identical or corresponding parts throughout the several views.

Figure 2:
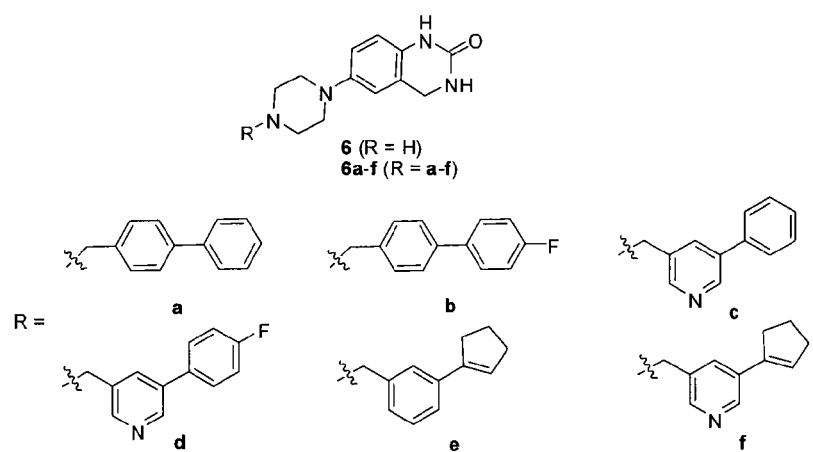
FIG. 2 displays a series of intermediate compounds.

In an ongoing effort to develop new antipsychotics (N. Ullah, Z. *Naturforsch.*, 67b, 75 (2012); N. Ullah, A. A. Q. Al-Shaheri, Z. *Naturforsch.*, 67b, 253 (2012); N. Ullah, J. Enz. Inhib. Med. Chem., doi:10.3109/14756366.2013.776556 (in press)—each incorporated herein by reference in its entirety), we have synthesized a series of 6-piperazinyl-3,4-dihydroquinazolin-2(1H)-ones (FIG. 2 displays compounds 6a-f). FIG. 2 displays the compounds.

In another embodiment, the compounds are used to treat schizophrenia by administering an effective amount of the compound to a patient suffering from schizophrenia. An effective amount of the compound includes but is not limited to using an amount of the compound in which the compound bears $D_2$ receptor antagonist properties and 5-$HT_{1A}$ receptor agonist properties sufficient enough to treat and/or alleviate symptoms of schizophrenia. Symptoms of schizophrenia include but are not limited to auditory hallucinations, visual hallucinations, olfactory hallucinations, gustatory hallucinations, hearing voices, delusions (often bizarre or persecutory in nature), disorganized thinking and speech, social withdrawal, sloppiness of dress and hygiene, loss of motivation and judgment, an observable pattern of emotional difficulty including lack of responsiveness, impairment in social cognition, paranoia, social isolation, difficulties in working and long-term memory, attention, executive functioning, remaining motionless in bizarre postures, exhibiting purposeless agitation, difficulty with facial emotion perception, manifestations of psychosis, expressing little emotion, inability to experience pleasure, and lack of desire to form relationships.

In another embodiment, the compound can be administered in an amount in the range of 1 mg-5000 mg, 5 mg-100 mg, 5 mg-20 mg, and 5-10 mg. Preferably, the compound is administered in a dose of 5-10 mg. The compound may be administered once a day or twice a day. Preferably the compound is administered once a day at the same time each day. The compound may be administered at any time period of the day.

In one embodiment of the invention, compositions containing one or more of the compounds can be delivered to a patient by systemic administration. Systemic administration is an in vivo systemic absorption or accumulation of drugs in the blood stream followed by distribution throughout the entire body. Administration routes that can lead to systemic absorption include but are not limited to intravenous, subcutaneous, intraperitoneal, inhalation, transdermal, oral, intrapulmonary and intramuscular routes.

In another embodiment, the compositions of the invention and formulations thereof can be administered orally, topically, parenterally, sublingually, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intradermal, intramuscular, or intrathecal injection or infusion techniques and the like.

The pharmaceutical compositions can be in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions and such compositions can contain one or more such sweetening agents, flavoring agents, coloring agents or preservative agents in order to provide pharmaceutically acceptable and palatable preparations. Tablets may contain the active ingredient or ingredients in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or *acacia*; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

In another embodiment, formulations for oral use can also be presented as hard gelatin capsules wherein the intermediate is mixed with an inert solid diluent including but not limited to calcium carbonate, calcium phosphate or kaolin, or as soft gelatin capsules wherein the intermediate is mixed with water or an oil medium including but not limited to peanut oil, liquid paraffin or olive oil.

In another embodiment, aqueous suspensions contain the active materials in a mixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum *acacia*; dispersing or wetting agents can be naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin. Oily suspensions can be formulated by suspending the active ingredients in a vegetable oil, for example *arachis* oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an antioxidant such as ascorbic acid.

In another embodiment, dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

In another embodiment, pharmaceutical compositions of the invention can also be in the form of oil-in-water emulsions. The oily phase can be a vegetable oil or a mineral oil or mixtures of these. Suitable emulsifying agents can be naturally-occurring gums, for example gum *acacia* or gum tragacanth, naturally-occurring phosphatides, for example soy bean lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In another embodiment, syrups and elixirs can be formulated with sweetening agents, for example glycerol, propylene glycol, sorbitol, glucose or sucrose. Such formulations can also contain a demulcent, a preservative and flavoring and coloring agents. The pharmaceutically acceptable compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

In another embodiment, the compositions can also be administered in the form of suppositories, e.g., for rectal administration of the drugs. These compositions can be prepared by mixing the drug with a suitable non-irritating excipient that is solid at ordinary temperatures but liquid at the rectal temperature and will therefore melt in the rectum to release the drug. Such materials include but are not limited to cocoa butter and polyethylene glycols.

EXAMPLES

General procedure: Melting Points were determined on a Büchi apparatus and are uncorrected. Elemental analysis was carried out on a Perkin Elmer Elemental Analyzer Series 11 Model 2400. IR spectra were recorded on a Perkin Elmer 16F PC FTIR spectrophotometer. $^1$H and $^{13}$C NMR spectra were measured in CDCl$_3$ and d$_6$-DMSO using TMS as internal standard on a JEOL LA 500 MHz spectrometer. Mass spectra were recorded on a GC-MS system (Agilent Technologies, 6890 N). Analytical TLC was carried out on silica gel 60 F$_{254}$ plates; column chromatography was carried out on Merck silica gel (200-400 mesh).

(5-Bromo-2-nitrophenyl)methanamine (13)

In a three neck round bottom flask solution of aldehyde 12 (3 g, 13.0 mmol) in THF (25 mL) was prepared at room temperature. To the solution were added ammonium hydroxide (28%, 5 mL) and sodium borohydride (1.47 g, 39 mmol) simultaneously in portions in such a rate that addition of both was completed in 20 minutes. The mixture was aged at room temperature for 4 h; ethyl acetate (30 mL) and brine (15 mL) were added. The organic layer was separated and washed with brine (15 mL), dried over Na$_2$SO$_4$ and evaporated to get an off-white solid, which was recrystallized from a mixture of ethanol and hexanes (3:7) to afford the title compound 13 as an off-white solid (2.68 g, 89%). IR (KBr) vmax. cm$^{-1}$: 3431, 3319 (NH$_2$), 3052 (Ar—H), 2925 (Alph-H), 1606, 1554 (C=C), 1521, 1432 (NO$_2$), 1230 (C—N), 1188 (C—O). $^1$H NMR (500 MHz, CDCl$_3$) δ=2.41 (br. s, 2H, NH$_2$), 5.02 (s, 2H, CH$_2$), 7.60 (dd, 1H, J=2.2, 8.2 Hz, H-4), 7.99 (m, 2H, aromatic H). $^{13}$C NMR (125.7 MHz, CDCl$_3$) δ=61.95 (CH$_2$), 126.51 (C-3), 129.53 (C-1), 131.45 (C-6), 132.50 (C-4), 139.00 (C-5), 145.99 (C-2). Calculated (%) for C$_7$H$_7$BrN$_2$O$_2$ (229.97); C, 36.39; H, 3.05; N, 12.12. found (%); C, 36.33; H, 3.10; N, 12.02.

N-(5-Bromo-2-nitrobenzyl)acetamide (14)

To a solution of compound 13 (2.5 g, 10.82 mmol) in pyridine (20 mL) was added acetic anhydride (2 mL, 21.60 mmol) and the mixture was stirred at room temperature for 12 h. The reaction was added ethyl acetate (30 mL) and the organic layer was washed sequentially with H$_2$O (20 mL), 1N HCl (15 mL×3), brine (15 mL) and dried over Na$_2$SO$_4$ and evaporated to get the title compound as an off-white solid (2.89 g, 98%). IR (KBr) vmax. cm$^{-1}$: 3419 (NH), 3062 (Ar—H), 2925 (Alph-H), 1695 (C=O), 1604, 1564 (C=C), 1520, 1435 (NO$_2$), 1232 (C—N), 1168 (C—O). $^1$H NMR (500 MHz, CDCl$_3$) δ=2.19 (s, 3H, CH$_3$); 5.50 (s, 2H, CH$_2$); 7.63 (dd, 1H, J=2.3, 8.6 Hz, H-4); 7.75 (d, 1H, J=2.3, H-6), 8.00 (d, 1H, J=8.6 Hz, H-3). $^{13}$C NMR (125.7 MHz, CDCl$_3$) δ=20.78 (CH$_3$), 62.27 (CH$_2$), 126.58 (C-3), 129.03 (C-1), 131.73 (C-6), 131.82 (C-4), 134.34 (C-5), 145.33 (C-2), 170.10 (CO). Calculated (%) for C$_9$H$_9$BrN$_2$O$_3$ (271.98); C, 39.58; H, 3.32; N, 10.26. found (%); C, 39.52; H, 3.36; N, 10.20.

tert-Butyl 4-(3-(acetamidomethyl)-4-nitrophenyl)-piperazine-1-carboxylate (15)

To an oven-dried flask, 1-boc-piperazine (3.19 g, 17.1 mmol), Cs$_2$CO$_3$ (5.82 g, 17.86 mmol), Pd$_2$(dba)$_3$ (1.44 g, 1.57 mmol), rac-2,2'bis(diphenylphosphino)-1,1'-binaphthyl (0.89 g, 1.43 mmol), toluene (8 mL) and compound 14 (3.89 g, 14.26 mmol) were added. While stirring the reaction mixture at room temperature, the air in the flask was removed and replaced by N$_2$. This process was repeated three times. The reaction temperature was brought to 110° C. and stirred for 8 h. Ethyl acetate (40 mL) was added to the mixture at room temperature, washed with H$_2$O (15 mL), brine (10 mL), dried over Na$_2$SO$_4$ and evaporated. The brown oily material was chromatographed on a silica column, eluting with hexanes: ethyl acetate (3:7) and then changing to (1:1) to obtain the title compound 15 as light yellow solid (3.88 g, 72%). IR (KBr) vmax. cm$^{-1}$: 3441 (NH), 3060 (Ar—H), 2963 (Alph-H), 1696 (C=O), 1607, 1577 (C=C), 1484, 1421 (NO$_2$), 1243

(C—N), 1168 (C—O). $^1$H NMR (500 MHz, CDCl$_3$) δ=1.49 (s, 9H, (C(CH$_3$)$_3$), 2.17 (s, 3H, CH$_3$), 3.42 (br. s, 4H, 2CH$_2$), 3.61 (br. s, 4H, 2CH$_2$), 5.54 (s, 2H, CH$_2$), 6.76 (dd, 1H, J=2.3, 9.3 Hz, H-6), 6.88 (br. s, 1H, H-2), 8.17 (d, 1H, J=9.4 Hz, H-5). $^{13}$C NMR (125.7 MHz, CDCl$_3$) δ=20.93 (CH$_3$), 28.39 (C(CH$_3$)$_3$), 46.82 (CH$_2$), 50.02 (CH$_2$), 66.12 (CH$_2$), 80.42 (C(CH$_3$)$_3$), 112.30 (aromatic-C), 112.48 (aromatic-C), 128.17 (aromatic-C), 135.60 (aromatic-C), 137.03 (aromatic-C), 153.02 (aromatic-C), 154.56 (CO), 170.29 (CO). Calculated (%) for C$_{18}$H$_{26}$N$_4$O$_5$ (378.19); C, 57.13; H, 6.93; N, 14.81. found (%); C, 57.07; H, 6.99; N, 14.71.

tert-butyl 4-(3-(acetamidomethyl)-4-aminophenyl) piperazine-1-carboxylate (16)

To a solution of compound 15 (1.13 g, 3 mmol) in EtOH (30 mL) was added Ra—Ni (0.20 g, 10% wet basis) and the mixture was subjected to hydrogenation in Parr apparatus at 20 psi for 6 hours. After filtering over the pad of celite, the solution was concentrated and purified over silica column, eluting with CH$_2$Cl$_2$:MeOH (95:5) and then changing to (92:8) afforded compound 16 as a light yellow thick oil (0.85 g, 82%). IR (KBr) vmax. cm$^{-1}$: 3441, 3421 (NH), 3042 (Ar—H), 2960 (Alph-H), 1699, 1696 (C═O), 1607, 1577 (C═C), 1240 (C—N), 1165 (C—O). $^1$H NMR (500 MHz, CDCl$_3$) δ=1.48 (s, 9H, (C(CH$_3$)$_3$), 2.16 (s, 3H, CH$_3$), 3.38 (br. s, 4H, 2CH$_2$), 3.52 (br. s, 4H, 2CH$_2$), 5.28 (br. s, 2H, NH$_2$), 5.49 (s, 2H, CH$_2$), 6.78 (dd, 1H, J=2.3, 9.3 Hz, H-6), 6.80 (br. s, 1H, H-2), 6.87 (d, 1H, J=9.2 Hz, H-5). $^{13}$C NMR (125.7 MHz, CDCl$_3$) δ=20.97 (CH$_3$), 28.35 (C(CH$_3$)$_3$), 42.53 (CH$_2$), 46.26 (CH$_2$), 62.54 (CH$_2$), 79.85 (C(CH$_3$)$_3$), 112.10 (aromatic-C), 112.38 (aromatic-C), 117.09 (aromatic-C), 130.22 (aromatic-C), 135.03 (aromatic-C), 143.02 (aromatic-C), 154.58 (CO), 170.51 (CO). Calculated (%) for C$_{18}$H$_{28}$N$_4$O$_3$ (348.22); C, 62.05; H, 8.10; N, 16.08. found (%); C, 62.00; H, 8.15; N, 16.00.

tert-Butyl 4-(4-amino-3-(aminomethyl)phenyl)piperazine-1-carboxylate (17)

To a solution of compound 16 (0.70 g, 2 mmol) in ethanol (20 mL) was added 4M solution of KOH in H$_2$O (4 mL, 16 mmol) and the mixture was stirred at 90° C. for 12 h. The mixture was concentrated under reduced pressure to get a brown oil material, which was resolved over silica column eluting with CH$_2$Cl$_2$:MeOH (95:5) and then changing to (90:10) to get compound 17 as light brown thick oil (0.51 g, 84%). IR (KBr) vmax. cm$^{-1}$: 3421, 3411 (NH), 3053 (Ar—H), 2936 (Alph-H), 1697 (C═O), 1606, 1578 (C═C), 1244 (C—N), 1166 (C—O). $^1$H NMR (500 MHz, CDCl$_3$) δ=1.47 (s, 9H, (C(CH$_3$)$_3$), 3.10 (br. s, 4H, 2CH$_2$), 3.22 (br. s, 4H, 2CH$_2$), 4.08 (s, 2H, CH$_2$), 4.58 (br. s, 2H, NH$_2$), 5.18 (br. s, 2H, NH$_2$), 6.68 (dd, 1H, J=2.3, 9.3 Hz, H-6), 6.73 (br. s, 1H, H-2), 6.81 (d, 1H, J=9.2 Hz, H-5). $^{13}$C NMR (125.7 MHz, CDCl$_3$) δ=28.05 (C(CH$_3$)$_3$), 42.43 (CH$_2$), 45.26 (CH$_2$), 50.54 (CH$_2$), 79.75 (C(CH$_3$)$_3$), 112.01 (aromatic-C), 112.08 (aromatic-C), 117.00 (aromatic-C), 130.28 (aromatic-C), 134.08 (aromatic-C), 143.08 (aromatic-C), 154.70 (CO). Calculated (%) for C$_{16}$H$_{26}$N$_4$O$_2$ (306.21); C, 62.72; H, 8.55; N, 18.29. found (%); C, 62.66; H, 8.62; N, 18.20.

tert-Butyl 4-(2-oxo-1,2,3,4-tetrahydroquinazolin-6-yl)piperazine-1-carboxylate (10)

To a solution of compound 17 (1.38 g, 4.5 mmol) in THF (20 mL) at room temperature was CDI (0.80 g, 4.95 mmol) and the reaction was stirred at 80° C. for 6 hr. The mixture was cooled to room temperature and the solid formed was filtered, washed with diethyl ether to afford 0.99 g (72%) of compound 10 as an off-white foam. IR (KBr) vmax. cm$^{-1}$: 3210, 3162 (NH), 3032 (Ar—H), 1691 (C═O), 1607, 1515, 1419 (C═C). $^1$H NMR (500 MHz, CDCl$_3$) δ=1.47 (s, 9H, (CH$_3$)$_3$C); 3.06 (m, 4H, 2CH$_2$); 3.52 (m, 4H, 2CH$_2$); 4.49 (s, 2H, CH$_2$); 6.69 (m, 2H, aromatic-H); 6.74 (m, 1H, aromatic-H); 7.82 (br.s, 1H, NH); $^{13}$C NMR (125.7 MHz, CDCl$_3$) δ=28.60 (CH$_3$)$_3$C), 43.35 (CH$_2$), 43.90 (CH$_2$), 50.66 (CH$_2$), 80.10 (CH$_3$)$_3$C), 112.11 (aromatic-C), 112.28 (aromatic-C), 117.19 (aromatic-C), 130.18 (aromatic-C), 134.88 (aromatic-C), 143.18 (aromatic-C), 154.62 (CO), 155.93 (C═O). Calculated (%) for C$_{17}$H$_{24}$N$_4$O$_3$ (332.18); C, 61.43; H, 7.28; N, 16.86. found (%) C, 61.38; H, 7.32; N, 16.81.

6-(piperazin-1-yl)-3,4-dihydroquinazolin-2(1H)-one (6)

To a solution of compound 10 (0.7 g, 2.11 mmol) in a mixture of CH$_2$Cl$_2$ (15 mL) and THF (5 mL) at 0° C. was added TFA (5 mL) and the mixture was stirred at room temperature for 6 h. The solvent was evaporated under vacuum to afford 0.66 g (96%) of compound 6 as a dark brown gum. $^1$H NMR (500 MHz, DMSO-d$_6$) δ=3.17 (m, 4H, 2CH$_2$), 3.40 (m, 4H, 2CH$_2$), 4.28 (s, 2H, CH$_2$), 6.70 (m, 2H, aromatic-H), 6.73 (m, 1H, aromatic-H), 8.81 (br. s, 1H, NH), 8.86 (br. s, 1H, NH). $^{13}$C NMR (125.7 MHz, DMSO-d$_6$) δ=46.11 (CH$_2$), 46.70 (CH$_2$), 48.68 (CH$_2$), 112.21 (aromatic-C), 112.27 (aromatic-C), 117.31 (aromatic-C), 130.28 (aromatic-C), 134.99 (aromatic-C), 143.38 (aromatic-C), 154.82 (C═O). Calculated (%) for C$_{14}$H$_{16}$F$_3$N$_4$O$_2$ (329.12); C, 51.06; H, 4.90; N, 17.01. found (%); C, 51.01; H, 4.95; N, 16.95.

6-(4-(biphenyl-4-ylmethyl)piperazin-1-yl)-3,4-dihydroquinazolin-2(1H)-one (6a)

Representative Procedure:
To a solution of compound 6 (0.15 g, 0.43 mmol) and biphenyl-4-carbaldehyde a (0.1 g, 0.55 mmol) in DMSO (2 mL) at 0° C. was added Et$_3$N (0.13 mL, 0.97 mmol). After being stirred for 0.5 h at room temperature, NaBH(OAc)$_3$ (0.11 g, 0.53 mmol) was added and the mixture was stirred for 6 h. The reaction was added sat. NaHCO$_3$ solution (5 mL) and stirred for 15 min, followed by the addition of ethyl acetate (20 mL). The organic layer was separated and washed with sat. NaHCO$_3$, brine, and dried over Na$_2$SO$_4$ and evaporated. Column chromatography on silica gel, eluting with methanol:dichloromethane (5:95) and then changing (10:90) afforded 0.102 g (60%) of compound 6a as an off-white solid. IR (KBr) vmax. cm$^{-1}$: 3436 (NH), 3052 (Ar—H), 2953 (Alph-H), 1702 (C═O), 1614, 1515, 1425 (C═C), 1229 (C—N), 1162 (C—O). $^1$H NMR (500 MHz, DMSO-d$_6$) δ=2.76 (m, 4H, 2CH$_2$), 3.18 (m, 4H, 2CH$_2$), 3.67 (s, 2H, CH$_2$), 4.49 (s, 2H, CH$_2$), 6.60 (d, 1H, J=2.3 Hz, aromatic H), 6.70 (dd, 1H, J=2.2, 8.5 Hz, aromatic H), 7.43-7.48 (m, 6H, aromatic H), 7.58-7.62 (m, 4H, aromatic H). $^{13}$C NMR (125.7 MHz, DMSO-d$_6$) δ=43.70 (CH$_2$), 48.23 (CH$_2$), 53.03 (CH$_2$), 62.64 (CH$_2$), 114.56 (aromatic-C), 117.64 (aromatic-C), 119.82 (aromatic-C), 124.58 (aromatic-C), 127.19 (aromatic-C), 127.26 (aromatic-C), 127.55 (aromatic-C), 127.90 (aromatic-C), 128.95 (aromatic-C), 129.26 (aromatic-C), 130.25 (aromatic-C), 130.59 (aromatic-C), 136.66 (aromatic-C), 138.22 (aromatic-C), 138.66 (aromatic-C), 140.95 (aromatic-C), 146.88 (aromatic-C), 156.32 (C═O). Calculated (%) for C$_{25}$H$_{26}$N$_4$O (398.21); C, 75.35; H, 6.58; N, 14.06. found (%); C, 75.27; H, 6.65; N, 13.96.

6-(4-((4'-fluorobiphenyl-4-yl)methyl)piperazin-1-yl)-3,4-dihydroquinazolin-2(1H)-one (6b)

Following the same procedure adopted for the synthesis of 6a, the reductive amination of compound 6 with aldehyde b afforded 0.101 g (55%) of compound 6b as an off-white solid. IR (KBr) vmax. cm$^{-1}$: 3421 (NH), 3048 (Ar—H), 2953 (Alph-H), 1702 (C=O), 1615, 1515, 1420 (C=C), 1228 (C—N), 1161 (C—O). $^1$H NMR (500 MHz, DMSO-d$_6$) δ=2.71 (m, 4H, 2CH$_2$), 3.17 (m, 4H, 2CH$_2$), 3.65 (s, 2H, CH$_2$), 4.43 (s, 2H, CH$_2$), 6.66 (d, 1H, J=2.3 Hz, aromatic H), 6.73 (dd, 1H, J=2.2, 8.5 Hz, aromatic H), 7.13-7.15 (m, 3H, aromatic H), 7.40-7.45 (m, 2H, aromatic H), 7.44-7.56 (m, 4H, aromatic H). $^{13}$C NMR (125.7 MHz, DMSO-d$_6$) δ=43.76 (CH$_2$), 48.28 (CH$_2$), 53.08 (CH$_2$), 62.66 (CH$_2$), 114.66 (aromatic-C), 115.29 (aromatic-C), 116.18 (aromatic-C), 117.69 (aromatic-C), 119.88 (aromatic-C), 124.65 (aromatic-C), 127.52 (aromatic-C), 129.39 (aromatic-C), 129.46 (aromatic-C), 130.85 (aromatic-C), 131.15 (aromatic-C), 136.69 (aromatic-C), 136.79 (aromatic-C), 138.79 (aromatic-C), 140.89 (aromatic-C), 146.89 (aromatic-C), 156.38 (C=O), 161.64 (aromatic-C). Calculated (%) for C$_{25}$H$_{25}$FN$_4$O (416.20); C, 72.09; H, 6.05; N, 13.45. found (%); C, 72.00; H, 6.11; N, 13.37.

6-(4-((5-phenylpyridin-3-yl)methyl)piperazin-1-yl)-3,4-dihydroquinazolin-2(1H)-one (6c)

Following the same procedure adopted for the synthesis of 6a, the reductive amination of compound 6 with aldehyde c afforded 0.082 g (48%) of compound 6c as light yellow gum. IR (KBr) vmax. cm$^{-1}$: 3436, 3192 (NH), 3042 (Ar—H), 2932 (Alph-H), 1690 (C=O), 1622, 1518, 1440 (C=C), 1175 (C—O). $^1$H NMR (500 MHz, CDCl$_3$) δ=2.72 (m, 4H, 2CH$_2$), 3.12 (m, 4H, 2CH$_2$), 3.62 (s, 2H, CH$_2$), 4.45 (s, 2H, CH$_2$), 6.64-6.72 (m, 3H, aromatic H), 7.10-7.13 (m, 2H, aromatic H), 7.40-7.42 (m, 2H, aromatic H), 7.44-7.48 (m, 3H, aromatic H), 7.62 (m, 2H, aromatic H), 7.91 (s, 1H, aromatic H), 8.55 (s, 1H, aromatic H), 8.92 (s, 1H, aromatic H). $^{13}$C NMR (125.7 MHz, CDCl$_3$) δ=43.67 (CH$_2$), 48.13 (CH$_2$), 52.92 (CH$_2$), 62.40 (CH$_2$), 114.46 (aromatic-C), 117.54 (aromatic-C), 119.70 (aromatic-C), 124.38 (aromatic-C), 126.94 (aromatic-C), 127.86 (aromatic-C), 128.38 (aromatic-C), 128.70 (aromatic-C), 128.78 (aromatic-C), 128.89 (aromatic-C), 132.98 (aromatic-C), 133.16 (aromatic-C), 136.18 (aromatic-C), 136.49 (aromatic-C), 136.60 (aromatic-C), 137.36 (aromatic-C), 146.10 (aromatic-C), 146.87 (aromatic-C), 148.86 (aromatic-C), 155.41 (C=O). Calculated (%) for C$_{24}$H$_{25}$N$_5$O (399.21); C, 72.16; H, 6.31; N, 17.53. found (%); C, 72.07; H, 6.37; N, 17.41.

6-(4-((5-(4-fluorophenyl)pyridin-3-yl)methyl)piperazin-1-yl)-3,4-dihydroquinazolin-2(1H)-one (6d)

Following the same procedure adopted for the synthesis of 6a, the reductive amination of compound 6 with aldehyde d afforded 0.083 g (49%) of compound 6d as a light yellow solid. IR (KBr) vmax. cm$^{-1}$: 3426, 3175 (NH), 3040 (Ar—H), 2962 (Alph-H), 1688 (C=O), 1622, 1525, 1420 (C=C), 1172 (C—O). $^1$H NMR (500 MHz, CDCl$_3$) δ=2.79 (m, 4H, 2CH$_2$), 3.19 (m, 4H, 2CH$_2$), 3.66 (s, 2H, CH$_2$), 4.48 (s, 2H, CH$_2$), 6.62-6.69 (m, 2H, aromatic H), 6.70-6.72 (m, 2H, aromatic H), 7.17 (m, 1H, aromatic H), 7.56-7.58 (m, 2H, aromatic H), 7.89 (s, 1H, aromatic H), 8.54 (s, 1H, aromatic H), 8.70 (s, 1H, NH), 8.96 (s, 1H, aromatic H). $^{13}$C NMR (125.7 MHz, CDCl$_3$) δ=43.60 (CH$_2$), 48.19 (CH$_2$), 52.90 (CH$_2$), 61.41 (CH$_2$), 114.32 (aromatic-C), 114.48 (aromatic-C), 115.85 (aromatic-C), 116.76 (aromatic-C), 117.54 (aromatic-C), 119.70 (aromatic-C), 124.38 (aromatic-C), 128.61 (aromatic-C), 129.75 (aromatic-C), 135.28 (aromatic-C), 136.63 (aromatic-C), 146.89 (aromatic-C), 146.96 (aromatic-C), 148.83 (aromatic-C), 150.49 (aromatic-C), 152.80 ((aromatic-C)), 155.06 (C=O), 161.73 (aromatic-C), 163.68 (aromatic-C). Calculated (%) for C$_{24}$H$_{24}$FN$_5$O (417.20); C, 69.05; H, 5.79; N, 16.78. found (%); C, 68.96; H, 5.86; N, 16.71.

6-(4-(3-cyclopentenylbenzyl)piperazin-1-yl)-3,4-dihydroquinazolin-2(1H)-one (6e)

Following the same procedure adopted for the synthesis of 6a, the reductive amination of compound 6 with aldehyde e afforded 0.111 g (60%) of compound 6e as light brown foam. IR (KBr) vmax. cm$^{-1}$: 3416, 3182 (NH), 3045 (Ar—H), 2933 (Alph-H), 1690 (C=O), 1622, 1518, 1421 (C=C), 1167 (C—O). $^1$H NMR (500 MHz, CDCl$_3$) δ=2.00-2.04 (m, 2H, CH$_2$), 2.51 (m, 2H, CH$_2$), 2.60 (m, 2H, 2CH$_2$), 2.73 (m, 4H, 2CH$_2$), 3.12 (m, 4H, 2CH$_2$), 3.60 (s, 2H, CH$_2$), 4.46 (s, 2H, CH$_2$), 6.19 (s, 1H, CH), 6.58-6.75 (m, 3H, aromatic H), 7.18 (m, 1H, aromatic H), 7.24 (m, 1H, aromatic H), 7.31 (m, 1H, aromatic H), 7.40 (s, 1H, aromatic H), 7.95 (br. s, 1H, NH). $^{13}$C NMR (125.7 MHz, CDCl$_3$) δ=23.52 (CH$_2$), 33.46 (CH$_2$), 33.58 (CH$_2$), 43.62 (CH$_2$), 48.18 (CH$_2$), 52.90 (CH$_2$), 62.48 (CH$_2$), 114.48 (aromatic-C), 115.12 (aromatic-C), 117.58 (aromatic-C), 119.72 (aromatic-C), 123.52 (aromatic-C), 124.42 (aromatic-C), 126.59 (aromatic-C), 128.06 (aromatic-C), 128.45 (aromatic-C), 130.07 (aromatic-C), 136.60 (aromatic-C), 137.79 (aromatic-C), 142.58 (aromatic-C), 146.92 (aromatic-C), 156.19 (C=O). Calculated (%) for C$_{24}$H$_{28}$N$_4$O (388.23); C, 74.20; H, 7.26; N, 14.42. found (%); C, 74.13; H, 7.33; N, 14.33.

6-(4-((5-cyclopentenylpyridin-3-yl)methyl)piperazin-1-yl)-3,4-dihydroquinazolin-2(1H)-one (6f)

Following the same procedure adopted for the synthesis of 6a, the reductive amination of compound 6 with aldehyde f afforded 0.090 g (54%) of compound 6f as an off-white solid. IR (KBr) vmax. cm$^{-1}$: 3412, 3190 (NH), 3061 (Ar—H), 2961 (Alph-H), 1690 (C=O), 1626, 1523, 1422 (C=C), 1170 (C—O). $^1$H NMR (500 MHz, CDCl$_3$) δ=2.00-2.06 (m, 2H, CH$_2$), 2.50 (m, 2H, CH$_2$), 2.61 (m, 2H, 2CH$_2$), 2.71 (m, 4H, 2CH$_2$), 3.15 (m, 4H, 2CH$_2$), 3.61 (s, 2H, CH$_2$), 4.45 (s, 2H, CH$_2$), 6.20 (s, 1H, CH), 6.58-6.75 (m, 3H, aromatic H), 6.78 (m, 1H, aromatic H), 7.71 (s, 1H, NH), 8.09 (s, 1H, aromatic H), 8.42 (s, 1H, aromatic H), 8.58 (s, 1H, aromatic H). $^{13}$C NMR (125.7 MHz, CDCl$_3$) δ=23.92 (CH$_2$), 33.56 (CH$_2$), 33.88 (CH$_2$), 43.69 (CH$_2$), 48.12 (CH$_2$), 52.92 (CH$_2$), 62.68 (CH$_2$), 114.43 (aromatic-C), 115.92 (aromatic-C), 117.44 (aromatic-C), 119.76 (aromatic-C), 124.39 (aromatic-C), 130.92 (aromatic-C), 133.09 (aromatic-C), 133.69 (aromatic-C), 136.60 (aromatic-C), 140.37 (aromatic-C), 146.90 (aromatic-C), 147.91 (aromatic-C), 149.46 (aromatic-C), 156.90 (C=O). Calculated (%) for C$_{23}$H$_{27}$N$_5$O (389.22); C, 70.92; H, 6.99; N, 17.98. found (%); C, 70.86; H, 7.06; N, 17.91.

To accomplish the synthesis of the desired compounds 6a-f, synthesis of the key intermediate (10) was required, which in turn was envision from the Buchwald-Hartwig coupling reaction of 6-bromo-3,4-dihydroquinazolin-2(1H)-one (9) (H. Venkatesan, F. M. Hocutt, T. K. Jones, M. H. Rabinowitz, *J. Org. Chem.*, 75, 3488 (2010)—incorporated herein by reference in its entirety) with tert-butyl piperazine-1-carboxylate. Thus the synthesis of compound (9) was commenced with the reduction of bromobenzonitrile with borane to afford diamine (8), which was reacted with triphosgene to get the desired bromide (9) in 23% overall yield from (7). However, the Buchwald-Hartwig coupling of bromides 9 with tert-butyl piperazine-1-carboxylate, under different reaction conditions (PdCl$_2$dppf, KOAc, DMF, 80° C.;

Pd(PPh$_3$)$_4$, toluene, ethanol, Na$_2$CO$_3$, reflux) were not successful; the desired 10 was not observed in any case (scheme 1).

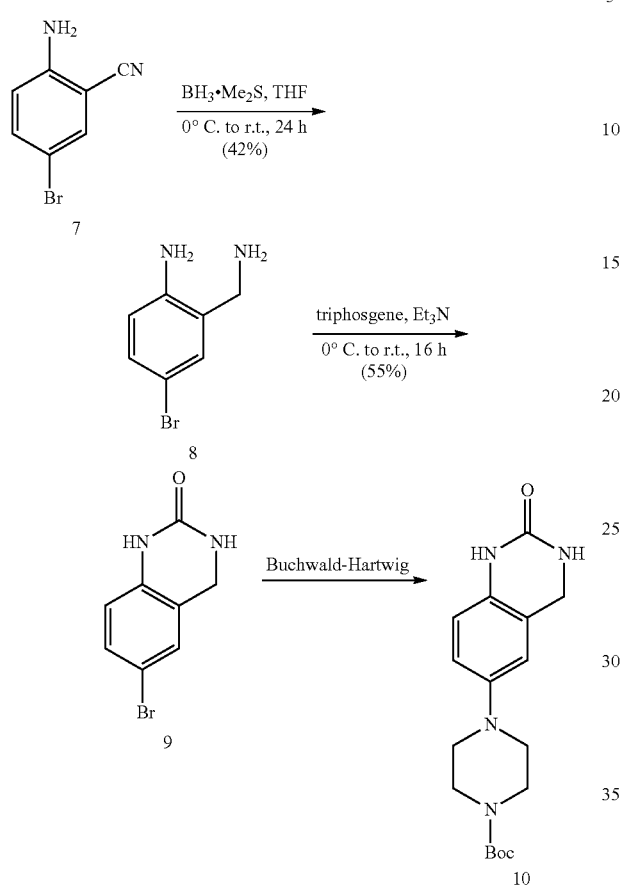

Therefore an alternative approach was adopted in which benzaldehyde 11 was nitrated to the known benzaldehyde 12, which in turn was subjected to reductive amination by condensing it with ammonium hydroxide, using sodium borohydride as reducing agent to produce amine 13 in high yield. Acetylation amine 13 generated acetamide 14, which was reacted with tert-butyl piperazine-1-carboxylate under Buchwald-Hartwig conditions to afford intermediate 15 in good yield. Reduction of nitro group of 15 over Pd—C in a Parr apparatus produced intermediate 16 in 91% yield high yield. Exposure of intermediate 16 under basic conditions rendered the desired diamine 17 in good yield after column purifications. Reaction of 17 with CDI in THF, heating the mixture at 80° C. for 6 hours, gave access to the key intermediate 10 in an overall yield of 33% from 14. Exposure of intermediate 10 to trifluoroacetic acid in a mixture of methanol and dichloromethane finally furnished the desired key intermediate 18 (scheme 2).

Scheme 2. Synthesis of intermediate 10, an alternative route

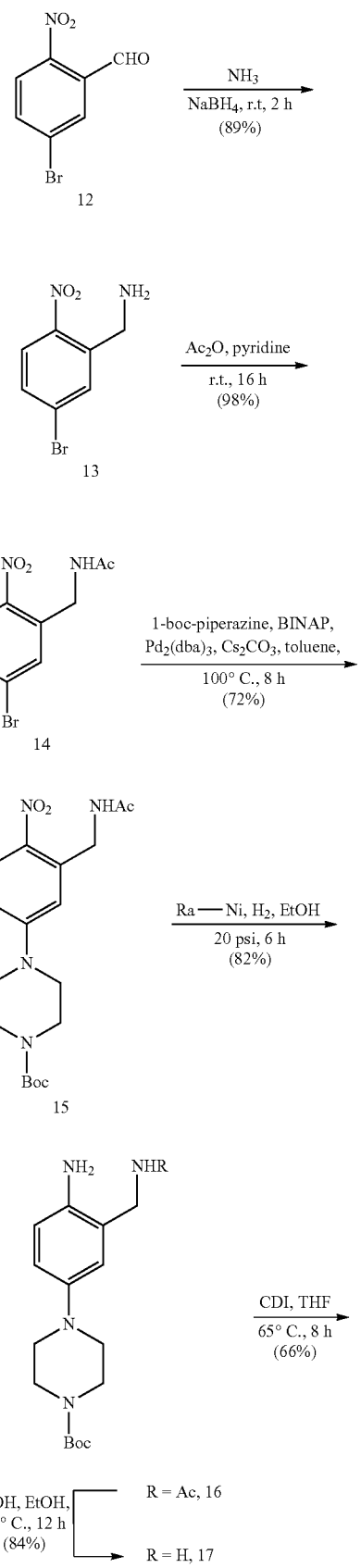

-continued

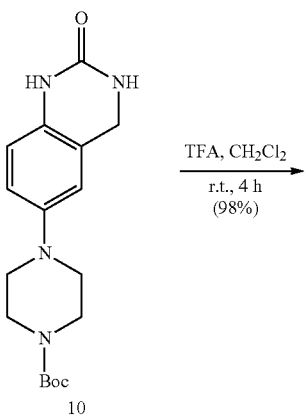

10

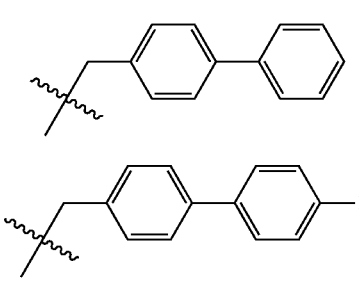

6

Having the desired intermediates 18 in hands, reductive amination of 18 with aldehydes (a-f)[15] in DMSO was performed, using NaBH(OAc)$_3$ as reducing agent to accomplish the synthesis of final compounds (6a-f) (scheme 3).

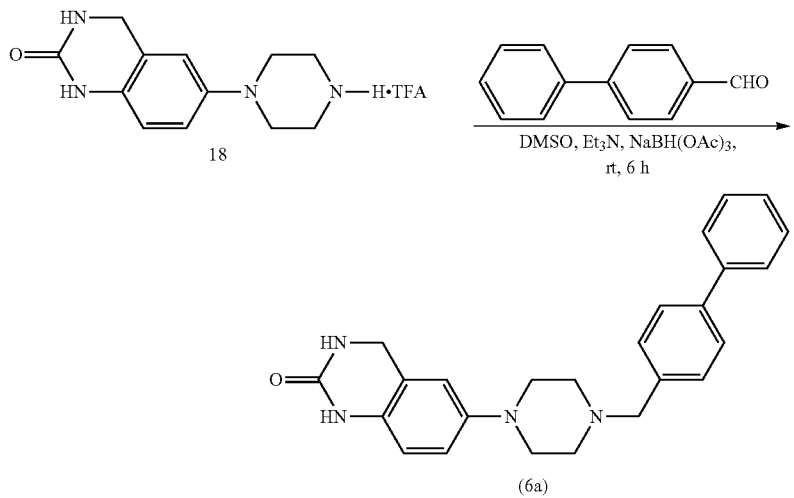

A series of new 6-piperazinyl-3,4-dihydroquinazolin-2 (1H)-ones bearing potent D$_2$ receptor antagonist and 5-HT$_{1A}$ receptor agonist properties have been synthesized.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A therapeutic agent comprising:
a dihydroquinazolinone compound of formula (I) or a pharmaceutically acceptable salt thereof as an active ingredient

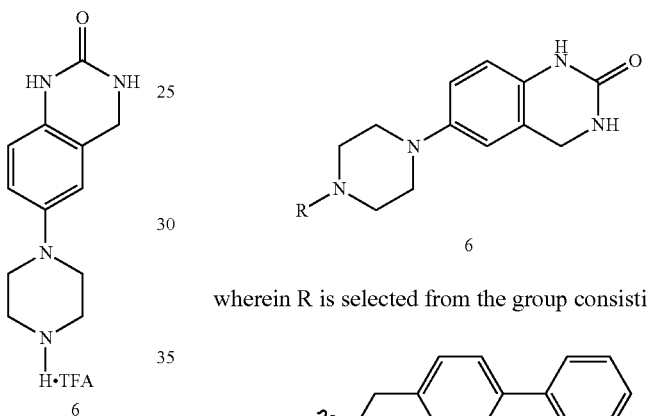

wherein R is selected from the group consisting of:

-continued

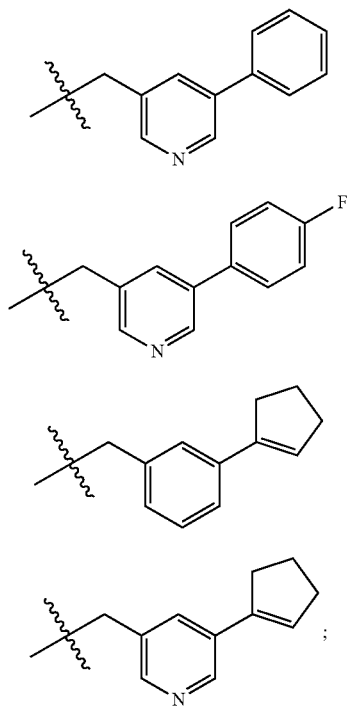

and
a pharmaceutically acceptable excipient selected from the group consisting of carboxymethylcellulose, methyl cellulose, hydropropylmethylcellulose, sodium alginate, polyvinylpyrrolidone, gum tragacanth, gum *acacia*, calcium carbonate, sodium carbonate, lactose, calcium phosphate, and sodium phosphate.

2. The therapeutic agent of claim 1, wherein R is:

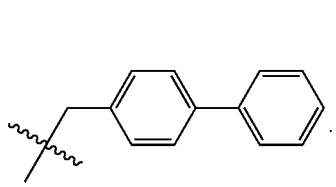

3. The therapeutic agent of claim 1, wherein R is:

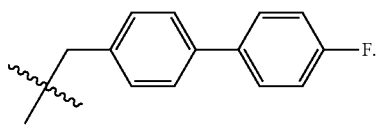

4. The therapeutic agent of claim 1, wherein R is:

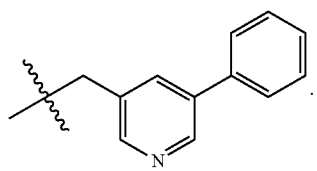

5. The therapeutic agent of claim 1, wherein R is:

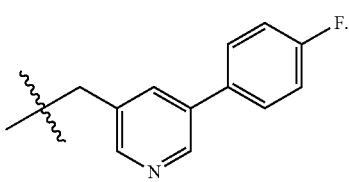

6. The therapeutic agent of claim 1, wherein R is:

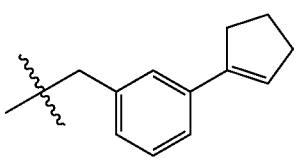

* * * * *